United States Patent

Assmann et al.

(10) Patent No.: US 6,521,653 B2
(45) Date of Patent: Feb. 18, 2003

(54) MICROBICIDAL BENZOTRIAZOLES

(75) Inventors: Lutz Assmann, Eutin (DE); Ralf Tiemann, Leverkusen (DE); Martin Kugler, Leichlingen (DE); Heinrich Schrage, Krefeld (DE); Klaus Stenzel, Düsseldorf (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/963,723

(22) Filed: Sep. 26, 2001

(65) Prior Publication Data

US 2002/0107398 A1 Aug. 8, 2002

Related U.S. Application Data

(62) Division of application No. 09/669,206, filed on Sep. 25, 2000, now Pat. No. 6,380,225, which is a division of application No. 09/296,843, filed on Apr. 22, 1999, now Pat. No. 6,172,092, which is a division of application No. 08/983,013, filed as application No. PCT/EP96/02611 on Jun. 17, 1996, now Pat. No. 5,985,903.

(30) Foreign Application Priority Data

Jun. 28, 1995 (DE) ......................................... 195 23 446

(51) Int. Cl.$^7$ ...................... A61N 31/427; C07D 417/12
(52) U.S. Cl. ...................... 514/369; 514/365; 548/182; 548/183; 548/186; 548/187; 548/202; 548/203; 548/204; 548/205
(58) Field of Search ................................ 514/365, 369; 548/182, 183, 186, 187, 202, 203, 204, 205

(56) References Cited

U.S. PATENT DOCUMENTS 3,740,396 A 6/1973 Haugwitz et al.

FOREIGN PATENT DOCUMENTS

| DE | 1046937 | 12/1958 |
|---|---|---|
| EP | 430471 | 6/1991 |
| EP | 462931 | 12/1991 |
| EP | 608753 | 8/1994 |
| EP | 238824 | 9/1997 |
| WO | 9425446 | 11/1994 |

OTHER PUBLICATIONS

N. Neykova, et al., Arzneimitell–Forschung, Bd. 31, Nr. 5, 1981, Aulendorf, DE, pp. 747–752, XP002013077, "Benzoxazolone–5'–sulphonanilides—activity".

A.J. Hubert, et al., Chemische Berichte, Bd. 103, Nr. 9, Sep. 1, 1970, Weinheim, DE, pp. 2828–2835, XP002013078, "Thermolyse und Photolyse vonBenzotriazolyl–(1)–Derivaten".

A.J. Hubert, et al. Journal of the Chemical Society, 1969, London, GB, "Photochemistry of benzotriazoles".

C.Corral, et al., Journal of Heterocyclic Chemistry, Bd. 24, Nr. 5, 1987, Provo US, pp. 1301–1303, XP002013080, Reactions of methyl 3–hydroxythiophene–2–carboxylate. Part 4. "Synghesis of methyl 5–azolyl–3–hydroxylthiophene–2–arboxylates".

A.R. Katritzky, et al., Heterocycles, Bd. 36, Nr. 6, Jun. 1, 1993, Tokyo, JP, pp. 1253–1262, XP002013081, "N–Sulfonybenzotriazoles. Part 2. Reactions of 1,1'–sulfonyldibenzotriazole and . . . triazoles".

A.R. Katrizky, et al., Tetrahedron, Bd. 48, Nr. 37, Sep. 11, 1992, Oxford, G.B. pp. 7817–7822, XP002013083. "Sulphonyl derivatives of benzotriazole: Part 1. A Novel approach . . . acids".

A.R. Katritzky, et al. Journal of Heterocyclic Chemistry, Bd. 31, Nr. 4, 1994, Provo, US pp. 757–763, XP002013082, "Chemistry of alpha–(benzotriazol–1–yl) . . . ring".

Database Crossfire, Beilstein Informationssysteme GmbH, Frankfurt DE XP002013084, siehe BRN=6211863, & Arch. Pharm., Bd. 312, 1988, pp. 463–467.

Database Crossfire, Beilstein Informationssysteme, GmbH, Frankfurt, DE XP002013086, siehe BRN=548444, 1000806, 541655, 543417, 543727 & Arch, Pharm. Ber-.Dtsch. Pharm. Ges., Bd. 303, Nr. 4, 1970, pp. 310–317.

Database Crossfire, Beilstein Informationssystem, GmbH, Frankfurt, DE, XP002013085, siehe BRN=202984 & J. Chem. Soc., Bd. 127, 1925, pp. 270, 2707.

Primary Examiner—Patricia L. Morris
(74) Attorney, Agent, or Firm—Norris McLaughlin & Marcus

(57) ABSTRACT

Novel benzotriazoles of the formula

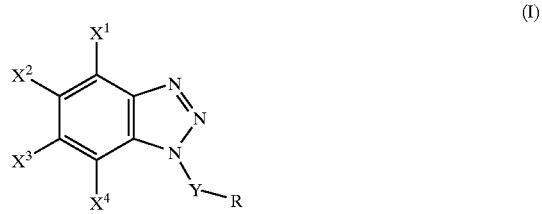

(I)

in which

R, $X^1$, $X^2$, $X^3$, $X^4$ and Y have the meanings given in the description, and their acid addition salts and metal salt complexes, a process for the preparation of these substances and their use as microbicides in crop protection and in material protection.

4 Claims, No Drawings

MICROBICIDAL BENZOTRIAZOLES

This is a division of U.S. Ser. No. 09/669,206, filed on Sep. 25, 2000, now U.S. Pat. No. 6,380,225, which is a division of U.S. Ser. No. 09/296,843, filed on Apr. 22, 1999, now U.S. Pat. No. 6,172,092, issued Jan. 9, 2001, which is a divisional of U.S. Ser. No. 08/983,013, filed on Dec. 19, 1997, now U.S. Pat. No. 5,985,903, issued Nov. 16, 1999, which is a 371 of PCT/EP96/02611 filed Jun. 17, 1996.

The present invention relates to novel benzotriazoles, a process for their preparation and their use as microbicides in crop protection and in protection of materials.

It has already been disclosed that certain benzotriazole derivatives have fungicidal properties (cf. DE-A 1-046 937, EP-A 0 238 824, EP-A 0 462 931, EP-A 0 549 532 and U.S. Pat. No. 2 943 017). The efficacy of the substances described there is good, but at low application rates leaves something to be desired.

Novel benzotriazoles have now been found of the formula

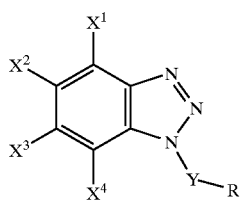
(I)

in which
X$^1$, X$^2$, X$^3$ and X$^4$, independently of each other, represent hydrogen, halogen, cyano, nitro, alkyl, halogenoalkyl, alkoxy, halogenoalkoxy, alkylthio, halogenoalkylthio, alkysulphinyl, halogenoalkylsulphinyl, alkylsulphonyl, halogenoalkylsulphonyl, unsubstituted or substituted cycloalkyl, hydroxycarbonyl alkylcarbonyl, alkoxycarbonyl, cycloalkylcarbonyl, cycloalkoxycarbonyl,

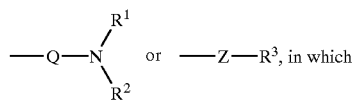

R$^1$ and R$^2$, independently of each other, represent hydrogen, alkyl, halogenoalkyl, alkoxyalkyl, alkylcarbonyl, unsubstituted or substituted aryl, unsubstituted or substituted arylcarbonyl, unsubstituted or substituted arylsulphonyl, unsubstituted or substituted arylaminocarbonyl or unsubstituted or substituted arylmethylsulphonyl or R$^1$ and R$^2$ together with the nitrogen atom to which they are bound represent a heterocyclic ring which may optionally be substituted by alkyl and may further contain an oxygen atom or an alkylimino group, Q represents a direct bond or a carbonyl group,
R$^3$ represents unsubstituted or substituted aryl or unsubstituted or substituted heterocyclyl and
Z represents a direct bond, CH$_2$, O, S, SO, SO$_2$ or CO or —CO—O—, where the oxygen atom is connected to the aryl or heterocyclyl radical, or
—SO$_2$—O—, where the sulphur atom is connected to the aryl or heterocyclyl radical, or
—S—CH$_2$—SO$_2$—, where the sulphur atom of the thio group is connected to the aryl or heterocyclyl radical, or X$^2$ and X$^3$ together represent an unsubstituted or substituted alkylene chain having 3 or 4 members in which one or two (non-adjacent) carbon atoms can be replaced by oxygen atoms, or X$^2$ and X$^3$ together represent a radical of the formula

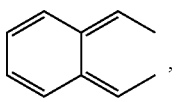

R represents unsubstituted or substituted heterocyclyl and
Y represents a direct bond, —CH$_2$—, —CH$_2$—CH$_2$—, —CO—, —SO$_2$—, —CO—O— or —SO—O—, where in the case of the two last-named groups, the carbon atom or the sulphur atom is connected to the nitrogen atom of the triazole ring,
and their acid addition salts and metal salt complexes.

Furthermore, it has been found that benzotriazoles of the formula (I) and their acid addition salts and metal salt complexes are obtained if benzotriazoles of the formula

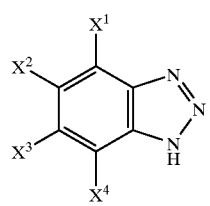
(II)

in which
X$^1$, X$^2$, X$^3$ and X$^4$ have the meanings given above, are reacted with halides of the formulas

 (III)

in which
R and Y have the meanings given above and
Hal represents chlorine or bromine,
in the presence or absence of an acid acceptor and in the presence or absence of a diluent and, if appropriate, an acid or a metal salt is added to the compounds of the formula (I) thus obtained.

Finally, it has been found that the benzotriazoles of the formula (I) and their acid addition salts and metal salt complexes possess very good microbicidal properties and can be used both in crop protection and in protection of materials.

Surprisingly, the substances of the invention show markedly better fungicidal activity than the previously known substances of the same indication most similar in terms of constitution.

The substances of the invention are generally defined by the formula (I).

X$^1$, X$^2$, X$^3$ and X$^4$, independently of each other, preferably represent hydrogen, fluorine, chlorine, bromine, iodine, cyano, nitro, straight-chain or branched alkyl having 1 to 8 carbon atoms, straight-chain or branched halogenoalkyl having 1 to 6 carbon atoms and 1 to 13 identical or different halogen atoms, straight-chain or branched alkoxy having 1 to 8 carbon atoms, straight-chain or branched halogenoalkoxy having 1 to 6 carbon atoms and 1 to 13 identical or different halogen atoms, straight-chain or branched alkylthio having 1 to 8 carbon atoms, straight-chain or branched halogenoalkylthio having 1 to 6 carbon atoms and 1 to 13 identical or different halogen atoms, straight-chain or branched alkylsulphinyl having 1 to 8 carbon atoms, straight-chain or branched halogenoalkylsulphinyl having 1 to 6 carbon atoms and 1 to 13 identical or different halogen atoms, straight-chain or branched alkylsulphonyl having 1 to 8 carbon atoms, straight-chain or branched halogenoalkylsulphonyl having 1 to 6 carbon atoms and 1 to 13 identical or different halogen atoms, cycloalkyl having 3 to 6 carbon atoms which may optionally be monosubstituted to penta-substituted, identically or differently, by halogen and/or alkyl having 1 to 4 carbon atoms, hydroxycarbonyl, alkylcarbonyl having 1 to 6 carbon atoms in the straight-chain or branched alkyl moiety, alkoxycarbonyl having 1 to 6 carbon atoms in the straight-chain or branched alkoxy moiety, cycloalkylcarbonyl having 3 to 6 carbon atoms in the cycloalkyl moiety, cycloalkoxycarbonyl having 3 to 6 carbon atoms in the cycloalkyl moiety,

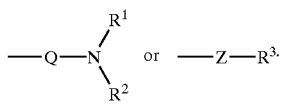

$R^1$ and $R^2$, independently of each other, preferably represent hydrogen, straight-chain or branched alkyl having 1 to 6 carbon atoms, straight-chain or branched halogenoalkyl having 1 to 6 carbon atoms and 1 to 13 identical or different halogen atoms, straight-chain or branched alkoxyalkyl having 1 to 4 carbon atoms in the alkoxy moiety and 1 to 4 carbon atoms in the alkyl moiety, alkylcarbonyl having 1 to 6 carbon atoms in the straight-chain or branched alkyl moiety, aryl having 6 to 10 carbon atoms, arylcarbonyl having 6 to 10 carbon atoms in the aryl moiety, arylsulphonyl having 6 to 10 carbon atoms, arylaminocarbonyl having 6 to 10 carbon atoms in the aryl moiety or arylmethylsulphonyl having 6 to 10 carbon atoms in the aryl moiety, where each of the aryl radicals mentioned above can be monosubstituted to trisubstituted, identically of differently, by halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, halogenoalkylthio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 4 carbon atoms and 1 to 5 identical or different halogen atoms and/or halogenoalkylsulphonyl having 1 to 4 carbon atoms and 1 to 5 identical or different halogen atoms.

$R^1$ and $R^2$, furthermore, together with the nitrogen atom to which they are bound preferably represent a heterocyclic ring having 5 or 6 ring members which may optionally be monosubstituted to trisubstituted by alkyl having 1 to 4 carbon atoms and can additionally contain an oxygen atom or a $C_1$–$C_4$-alkylimino group.

Q also preferably represents a direct bond or a carbonyl group.

$R^3$ preferably represents aryl having 6 to 10 carbon atoms, where each of these radicals can be monosubstituted to trisubstituted, identically or differently, by halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, halogenoalkylthio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 4 carbon atoms and 1 to 5 identical or different halogen atoms and/or halogenoalkylsulphonyl having 1 to 4 carbon atoms and 1 to 5 identical or different halogen atoms, or $R^3$ preferably represents a saturated or unsaturated heterocyclyl radical having 5 or 6 ring members and 1 to 3 hetero atoms, such as nitrogen, oxygen and/or sulphur, where these radicals can be monosubstituted to trisubstituted, identically or differently, by halogen, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 3 carbon atoms in the alkoxy moiety, cycloalkyl having 3 to 6 carbon atoms, cyano and/or nitro.

Z also preferably represents a direct bond or $CH_2$, O, S, SO, $SO_2$, CO, or
—CO—O—, where the oxygen atom is connected to the aryl or heterocyclyl radical, or
—$SO_2$—O—, where the sulphur atom is connected to the aryl or heterocyclyl radical, or
—S—$CH_2$—$SO_2$—, where the sulphur atom of the thio group is connected to the aryl or heterocyclyl radical.

$X^2$ and $X^3$ also together preferably represent an alkylene chain having 3 or 4 members which is optionally monosubstituted to hexasubstituted by halogen, alkyl having 1 to 4 carbon atoms and/or halogenoalkyl having 1 to 4 carbon atoms and 1 to 9 halogen atoms, and in which alkylene chain one or two (non-adjacent) carbon atoms can be replaced by oxygen atoms, or $X^2$ and $X^3$ together represent a radical of the formula

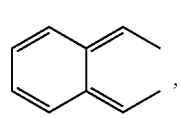

R preferably represents a saturated or unsaturated, optionally benzannelated heterocyclyl radical having 5 or 6 ring elements and 1 to 3 hetero atoms, such as nitrogen, oxygen and/or sulphur, where these radicals can be monosubstituted to trisubstituted, identically or differently, by halogen, cyano, nitro, hydroxyl, amino, formyl, carboxyl, carbamoyl, thiocarbamoyl, alkyl having 1 to 4 carbon atoms, alkoxy having 1 to 4 carbon atoms, halogeno alkyl having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkoxycarbonyl having 1 to 4 carbon atoms in the alkoxy moiety, cycloalkyl having 3 to 6 carbon atoms, halogenoalkylsulphinyl having 1 to 4 carbon atoms and 1 to 5 identical or different halogen atoms, halogenoalkylsulphonyl having 1 to 4 carbon atoms and 1 to 5 identical or different halogen atoms, alkylamino having 1 to 4 carbon atoms, hydroxyalkylamino having 1 to 4 carbon atoms, dialkylamino having 1 to 4 carbon atoms in each alkyl group, alkylcarbonyl having 1 to 4 carbon atoms in the alkyl moiety, alkylcarbonylamino having 1 to 4 carbon atoms in the alkyl moiety, hydroxyiminoalkyl having 1 to 4 carbon atoms in the alkyl moiety, alkoxyiminoalkyl having 1 to 4 carbon atoms in the alkoxy moiety and 1 to 4 carbon atoms in the alkyl moiety, alkylcarbonyloxy having 1 to 4 carbon atoms in the alkyl moiety and/or halogenoalkylcarbonyloxy having 1 to 4 carbon atoms in the halogenoalkyl group and 1 to 5 identical or different halogen atoms, and where the heterocyclyl radicals can also contain oxo groups.

Y also preferably represents a direct bond, $CH_2$, $CH_2$—$CH_2$, CO, $SO_2$, —CO—O— or —SO—O—, where in the case of the two last named groups, the carbon atom or the sulphur atom, respectively, is connected to the nitrogen atom of the triazole ring.

$X^1$, $X^2$, $X^3$ and $X^4$, independently of each other, particularly preferably represent hydrogen, fluorine, chlorine, bromine, iodine, cyano, nitro, straight-chain or branched alkyl having 1 to 6 carbon atoms, halogenoalkyl having 1 or 2 carbon atoms and 1 to 5 fluorine, chlorine and/or bromine atoms, straight-chain or branched alkoxy having 1 to 6 carbon atoms, halogenoalkoxy having 1 or 2 carbon atoms and 1 to 5 fluorine, chlorine and/or bromine atoms, straight-chain or branched alkylthio having 1 to 6 carbon atoms, halogenoalkylthio having 1 or 2 carbon atoms and 1 to 5 fluorine, chlorine and/or bromine atoms, straight-chain or branched alkylsulphinyl having 1 to 6 carbon atoms, halogenoalkylsulphinyl having 1 or 2 carbon atoms and 1 to 5 fluorine, chlorine and/or bromine atoms, straight-chain or branched alkylsulphonyl having 1 to 6 carbon atoms, halogenoalkylsulphonyl having 1 or 2 carbon atoms and 1 to 5 fluorine, chlorine and/or bromine atoms, cycloalkyl having 3 to 6 carbon atoms which is optionally monosubstituted to trisubstituted, identically or differently, by fluorine, chlorine, bromine, methyl and/or ethyl, hydroxycarbonyl, alkylcarbonyl having 1 to 4 carbon atoms in the straight-chain or branched alkyl moiety, alkoxycarbonyl having 1 to 4 carbon atoms in the straight-chain or branched alkoxy moiety, cycloalkylcarbonyl having 3 to 6 carbon atoms in the cycloalkyl moiety, cycloalkoxycarbonyl having 3 to 6 carbon atoms in the cycloalkyl moiety,

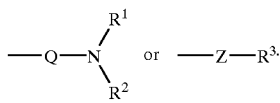

$R^1$ and $R^2$, independently of each other, particularly preferably represent hydrogen, straight-chain or branched alkyl having 1 to 4 carbon atoms, halogenoalkyl having 1 or 2 carbon atoms and 1 to 5 fluorine, chlorine and/or bromine atoms, straight-chain or branched alkoxyalkyl having 1 to 3 carbon atoms in the alkoxy moiety and 1 to 3 carbon atoms in the alkyl moiety, alkylcarbonyl having 1 to 4 carbon atoms in the straight-chain or branched alkyl moiety, phenyl, phenylcarbonyl, phenylsulphonyl, phenylaminocarbonyl or phenylmethylsulphonyl, where each of the phenyl radicals named above can be monosubstituted to trisubstituted, identically or differently, by fluorine, chlorine, bromine, cyano, nitro, alkyl having 1 or 2 carbon atoms, alkoxy having 1 or 2 carbon atoms, alkylthio having 1 or 2 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, halogenoalkylthio having 1 of 2 carbon atoms and 1 to 5 fluorine, chlorine and/or bromine atoms, alkylsulphinyl having 1 or 2 carbon atoms, alkylsulphonyl having 1 or 2 carbon atoms, halogenoalkylsulphinyl having 1 or 2 carbon atoms and 1 to 5 fluorine, chlorine and/or bromine atoms and/or halogenoalkylsulphonyl having 1 or 2 carbon atoms and 1 to 5 fluorine, chlorine and/or bromine atoms.

$R^1$ and $R^2$, furthermore, together with the nitrogen atom to which they are bound also particularly preferably represent a saturated heterocyclic ring having 5 or 6 ring members which is optionally monosubstituted to trisubstituted by methyl and/or ethyl, where one carbon atom of the ring can be replaced by oxygen or methylimino.

Q also particularly preferably represents a direct bond or a carbonyl group.

$R^3$ particularly preferably represents phenyl which can be monosubstituted to trisubstituted, identically or differently, by fluorine, chlorine, bromine, cyano, nitro, alkyl having 1 or 2 carbon atoms, alkoxy having 1 or 2 carbon atoms, alkylthio having 1 or 2 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, halogenoalkylthio having 1 or 2 carbon atoms and 1 to 5 fluorine, chlorine and/or bromine atoms, alkylsulphinyl having 1 or 2 carbon atoms, alkylsulphonyl having 1 or 2 carbon atoms, halogenoalkylsulphinyl having 1 or 2 carbon atoms and 1 to 5 fluorine, chlorine and/or bromine atoms and/or halogenoalkylsulphonyl having 1 or 2 carbon atoms and 1 to 5 fluorine, chlorine and/or bromine atoms, or $R^3$ particularly preferably represents a saturated or unsaturated heterocyclyl radical having 5 or 6 ring members and 1 to 3 hetero atoms, such as nitrogen, oxygen and/or sulphur, where these radicals can be monosubstituted to trisubstituted, identically or differently, by fluorine, chlorine, bromine, alkyl having 1 or 2 carbon atoms, alkoxy having 1 or 2 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, alkoxycarbonyl having 1 or 2 carbon atoms in the alkoxy moiety, cycloalkyl having 3 to 6 carbon atoms, cyano and/or nitro.

Z also particularly preferably represents a direct bond or $CH_2$) O, S, SO, $SO_2$, CO, or
—CO—O—, where the oxygen atom is connected to the phenyl or heterocycly radical, or
—$SO_2$—O—, where the sulphur atom is connected to the phenyl or heterocyclyl radical, or
—S—$CH_2$—$SO_2$—, where the sulphur atom of the thio group is connected to the phenyl or heterocyclyl radical.

$X^2$ and $X^3$ also together particularly preferably represent an alkylene chain having 3 or 4 members which is optionally monosubstituted to hexasubstituted by fluorine, chlorine, methyl and/or trifluoromethyl, in which alkylene chain one or two (non-adjacent) carbon atoms can be replaced by oxygen, or $X^2$ and $X^3$ together represent a radical of the formulae

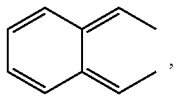

R particularly preferably represents a saturated or unsaturated, optionally benzannelated heterocyclyl radical having 5 or 6 ring members and 1 to 3 hetero atoms, such as nitrogen, oxygen and/or sulphur, where these radicals can be monosubstituted to trisubstituted, identically or differently, by fluorine, chlorine, bromine, cyano, nitro, hydroxyl, amino, formyl, carboxyl, carbamoyl, thiocarbamoyl, alkyl having 1 to 4 carbon atoms, alkoxy having 1 to 4 carbon atoms, halogenoalkyl having 1 or 2 carbon atoms and 1 to 5 fluorine, chlorine and/or bromine atoms, halogenoalkoxy having 1 or 2 carbon atoms and 1 to 5 fluorine, chlorine and/or bromine atoms, alkoxycarbonyl having 1 or 2 carbon atoms in the alkoxy moiety, cycloalkyl having 3 to 6 carbon atoms, halogenoalkylsulphinyl having 1 or 2 carbon atoms and 1 to 5 fluorine, chlorine and/or bromine atoms, halogenoalkylsulphonyl having 1 or 2 carbon atoms and 1 to 5 fluorine, chlorine and/or bromine atoms, alkylamino having 1 or 2 carbon atoms, hydroxyalkylamino having 1 or 2 carbon atoms, dialkylamino having 1 or 2 carbon atoms in each alkyl group, alkylcarbonyl having 1 or 2 carbon atoms in the alkyl moiety, alkylcarbonylamino having 1 to 3 carbon atoms in the alkyl moiety, hydroxyiminoalkyl having 1 or 2 carbon atoms in the alkyl moiety, alkoxyiminoalkyl having 1 or 2 carbon atoms in the alkoxy moiety and 1 or 2 carbon atoms in the alkyl moiety, alkylcarbonyloxy having 1 or 2 carbon atoms in the alkyl group and/or halogenoalkylcarbonyloxy having 1 or 2 carbon atoms in the halogenoalkyl group and 1 to 5 fluorine, chlorine and/or bromine atoms, and where the heterocyclyl radicals can also contain one or two oxo groups.

Y also particularly preferably represents a direct bond, $CH_2$, $CH_2$—$CH_2$, CO, $SO_2$, —CO—O— or —SO—O—, where in the case of the two last-named groups, the carbon atom or the sulphur atom, respectively, is connected to the nitrogen atom of the triazole ring.

$X^1$, $X^2$, $X^3$ and $X^4$, independently of each other, very particularly preferably represent hydrogen, fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulphonyl, acetyl, acetyloxy, methoxycarbonyl, ethoxycarbonyl, cyclopropyl, cyclohexyl,

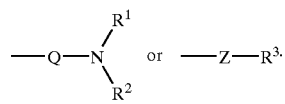

$R^1$ and $R^2$, independently of each other, very particularly preferably represent hydrogen, methyl, ethyl, n-propyl, isopropyl or phenyl.

$R^1$ and $R^2$, furthermore, also together with the nitrogen atom to which they are bound very particularly preferably represent pyrrolidinyl, piperidinyl, morpholinyl or 4-methyl-piperazinyl.

Q also very particularly preferably represents a direct bond or a carbonyl group.

$R^3$ very particularly preferably represents phenyl which can be monosubstituted to trisubstituted, identically or differently, by fluorine, chlorine, bromine, cyano, nitro, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, difluoromethylsulphinyl and/or trifluoromethylsulphonyl, or $R^3$ very particularly preferably represents pyrrolyl, furyl, thienyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5-triazinyl, pyridinyl, pyrimidinyl, pyrazinyl or pyridazinyl, where these radicals can be monosubstituted to trisubstituted, identically or differently, by fluorine, chlorine, methyl, methoxy, trifluoromethyl and/or trifluoromethoxy.

Z also very particularly preferably represents a direct bond or $CH_2$, O, S, SO, $SO_2$, CO, or
—CO—O—, where the oxygen atom is connected to the phenyl or heterocyclyl radical, or
—$SO_2$—O—, where the sulphur atom is connected to the phenyl or heterocyclyl radical, or
—S—$CH_2$—$SO_2$—, where the sulphur atom of the thio group is connected to the phenyl or heterocyclyl radical.

$X^2$ and $X^3$ also together very particularly preferably represent the groups —O—$CF_2$—O—, —O—$CF_2$—CHF—O—, —O—CHF—CHF—O—, —O—$CF_2$—$CF_2$—O—, —O—$CF_2$—CFCl—O—, —O—CFCl—CFCl—O—, —$(CH_2)_3$—, —$C(CH_3)_2$—$CH_2$—$C(CH_3)_2$— or

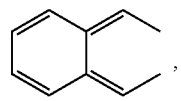

R very particularly preferably represents pyrrolyl, furyl, thienyl, pyrazolyl, imidazolyl, thiazolyl, isothiazolyl, oxazolyl, isoxazolyl, oxadiazolyl, thiadiazolyl, 1,2,3-triazinyl, 1,2,4-triazinyl, 1,3,5-triazinyl, pyridinyl, pyrimidinyl, pyrazinyl, pyridazinyl, benzofuryl, benzothienyl, quinolyl or the radicals of the formulae

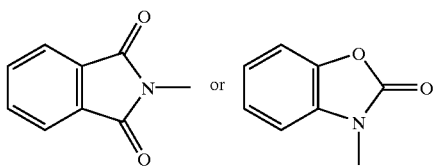

where these radicals can be monosubstituted to trisubstituted, identically or differently, by fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulphonyl, cyclopropyl, methylamino, ethylamino, n- or i-propylamino, dimethylamino, diethylamino, acetyl, propionyl, methylcarbonylamino, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl and/or ethoxyiminoethyl.

Y also very particularly preferably represents a direct bond, CH$_2$, CH$_2$—CH$_2$, CO, SO$_2$, —CO—O— or —SO—O—, where in the case of the two last mentioned groups, the carbon atom or the sulphur atom, respectively, is connected to the nitrogen of the triazole ring.

Preferred compounds of the invention are also addition products from acids and those benzotriazoles of the formula (I), in which R, $X^1$, $X^2$, $X^3$, $X^4$ and Y have the meanings which have been mentioned for these radicals as preferred.

The acids which can be added preferably include hydrohalic acids, such as hydrochloric acid and hydrobromic acid, in particular hydrochloric acid, in addition phosphoric acid, nitric acid, mono- and bifunctional carboxylic acids and hydroxycarboxylic acids, such as acetic acid, maleic acid, succinic acid, fumaric acid, tartaric acid, citric acid, salicylic acid, sorbic acid and lactic acid, and sulphonic acids, such as p-toluenesulphonic acid, 1,5-naphthalenedisulphonic acid and, furthermore, saccharin and thiosaccharin.

Furthermore, preferred compounds of the invention are addition products from salts of metals of groups II to IV and subgroups I and II and IV to VIII of the Periodic Table of the Elements and those benzotriazoles of the formula (I) in which R, $X^1$, $X^2$, $X^3$, $X^4$ and Y have the meanings which have been mentioned as preferred for these radicals.

In this case, salts of copper, zinc, manganese, magnesium, tin, iron and nickel are particularly preferred. Anions of these salts which are useful are those which are derived from those acids which lead to physiologically tolerated addition products. Particularly preferred acids of this type are, in this context, the hydrohalic acids, such as hydrochloric acid and hydrobromic acid, in addition phosphoric acid, nitric acid and sulphuric acid.

Examples of substances of the invention which may be mentioned are the benzotriazoles listed in Tables 1 to 8.

TABLE 1

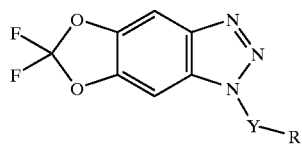

(Ia)

where —Y—R represents the following substituents:

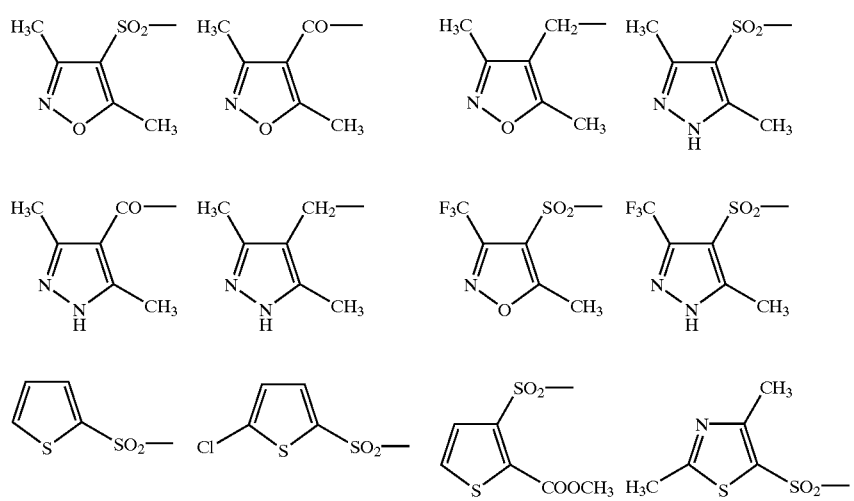

TABLE 1-continued

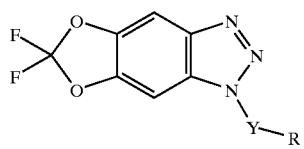
(Ia)

where —Y—R represents the following substituents:

TABLE 2

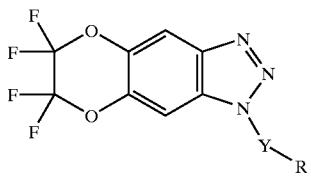
(Ib)

where —Y—R represents the substituents mentioned in Table 1.

TABLE 3

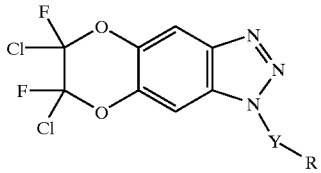
(Ic)

where —Y—R represents the substituents mentioned in Table 1.

TABLE 4

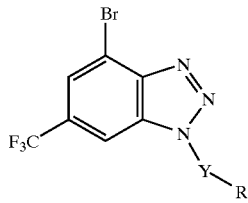
(Id)

where —Y—R represents the substituents mentioned in Table 1.

TABLE 5

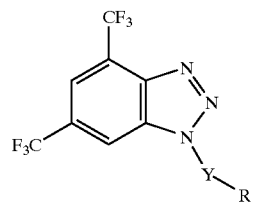
(Ie)

where —Y—R represents the substituents mentioned in Table 1.

TABLE 6

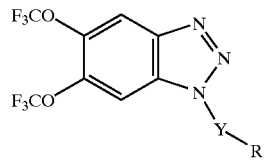
(If)

where —Y—R represents the substituents mentioned in Table 1.

TABLE 7

(Ig)

where —Y—R represents the substituents mentioned in Table 1.

TABLE 8

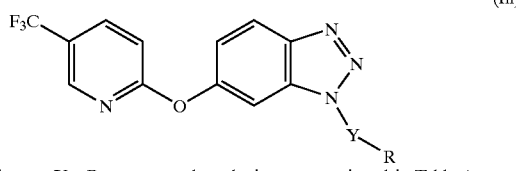

(Ih)

where —Y—R represents the substituents mentioned in Table 1.

If 6,6-difluoro-[1,3]dioxolo-[4,5-f]-1H-benzotriazole and 3,5-dimethylisoxazole-4-sulphonyl chloride are used as starting materials, the course of the process of the invention can be illustrated by the formula scheme below:

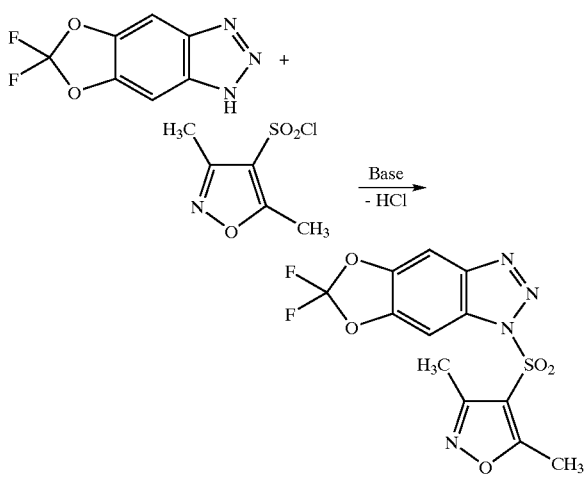

The benzotriazoles required as starting materials to carry out the process of the invention are generally defined by the formula (II). In this formula, $X^1$, $X^2$, $X^3$ and $X^4$ preferably have the meanings which. have already been mentioned as preferred for these radicals in connection with the description of the substances of the invention of the formula (I).

The benzotriazoles of the formula (II) are known or may be prepared by methods known in principle (cf. Chem. Reviews, 1950, 1; DE-A 3 406 011 and EP-A 0 608 573).

The halides additionally required as starting materials to carry out the process of the invention are generally defined by the formula (III). In this formula, R and Y preferably have those meanings which have already been mentioned as preferred for these radicals in connection with the description of the substances of the invention of the formula (I). Hal represents chlorine or bromine.

The halides of the formula (III) are known or may be prepared by known methods.

Diluents which can be used when the process of the invention is carried out are all conventional inert, organic solvents. Those which can preferably be used are aliphatic, cycloaliphatic and aromatic, optionally halogenated hydrocarbons, such as benzine, benzene, toluene, xylene, chlorobenzene, dichlorobenzene, petroleum ether, hexane, cyclohexane, dichloromethane, chloroform or carbon tetrachloride; in addition ethers, such as diethyl ether, diisopropyl ether, dioxane, tetrahydrofuran or ethylene glycol dimethyl ether or ethylene glycol diethyl ether, in addition ketones, such as acetone or butanone or methyl isobutyl ketone; nitriles such as acetonitrile, propionitrile or benzonitrile, or esters such as methyl acetate or ethyl acetate.

The process of the invention is preferably carried out in the presence of an acid acceptor. Those which are suitable are all conventional inorganic or organic bases. Those which preferably can be used are alkaline earth metal hydroxides or alkali metal hydroxides such as sodium hydroxide, calcium hydroxide, potassium hydroxide, or else ammonium hydroxide, alkali metal carbonates, such as sodium carbonate, potassium carbonate, potassium hydrogencarbonate, sodium hydrogen-carbonate, alkali metal acetates or alkaline earth metal acetates such as sodium acetate, potassium acetate, calcium acetate, and tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

The reaction temperatures can be varied within a relatively broad range when the process of the invention is carried out. Generally, temperatures between 0 and 150° C. are employed, preferably temperatures between 20 and 120° C.

The process of the invention is usually carried out at atmospheric pressure. However, it is also possible to employ elevated or reduced pressure.

To carry out the process of the invention, per mole of benzotriazole of the formula (II) in a diluent, generally 1.0 to 2.0 mol, preferably 1.0 to 1.3 mol, of halide of the formula (III) are used and, if appropriate, 1.0 to 2.0 mol, preferably 1.0 to 1.3 mol, of acid acceptor. The reaction conditions, workup and isolation of the reaction products are in accordance with known processes (cf. also the preparation examples).

The benzotriazoles of the formula (I) can be converted into acid addition salts or metal salt complexes.

To prepare acid addition salts of the compounds of the formula (I), those acids are preferably used which have already been mentioned as preferred acids in connection with the description of the acid addition salts of the invention.

The acid addition salts of the compounds of the formula (I) can be obtained in a simple manner by conventional salt-formation methods, e.g. by dissolving a compound of the formula (I) in a suitable inert solvent and adding the acid, e.g. hydrochloric acid, and can be isolated in a known manner, e.g. by filtering off, and, if appropriate, can be purified by washing with an inert organic solvent.

To prepare metal salt complexes of the compounds of the formula (I), those salts of metals are preferably used which have already been mentioned as preferred metal salts in connection with the description of the metal salt complexes of the invention.

The metal salt complexes of the compounds of the formula (I) can be obtained in a simple manner by conventional processes, e.g. by dissolving the metal salt in alcohol, e.g. ethanol, and adding it to compounds of the formula (I). Metal salt complexes can be isolated in a known manner, e.g. by filtering off, and, if appropriate, can be purified by recrystallization.

The active compounds of the invention have a strong microbicidal activity and can be used to control undesirable microorganisms, such as fungi and bacteria, in crop protection and in protection of materials.

The undesirable microorganisms include fungi, such as Plasmodiophoromycetes, Oomycetes, Chytridiomycetes, Zygomycetes, Ascomycetes, Basidiomycetes, Deuteromycetes and, in addition, bacteria, such as Pseudomonadaceae, Rhizobiaceae, Enterobacteriaceae, Corynebacteriaceae and Streptomycetaceae.

Some causative organisms of fungal and bacterial disorders included among the generic terms listed above which may be mentioned by way of example but not as a restriction are:

Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubensis;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminea;* (conidial form: Drechslera, Syn: Helminthosporium);
Cochliobolus species, such as *Cochliobolus sativus;* (conidial form: Drechslera, Syn: Helminthosporium);
Uromyces species, such as *Uromyces appendiculatus;*
Puccinia species, such as *Puccinia recondita;*
Tilletia species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae;*
Pseudocercosporella species, such as *Pseudocercosporella herpotrichoides.*

The high compatibility with plants of the active compounds in the concentrations necessary to control plant diseases permits treatment of above ground plant parts, of planting material and seed material and of the soil.

The active compounds of the invention can be used with particularly high success for controlling diseases in fruit and vegetable cultivation and viticulture, such as against Phytophthora or Plasmopara species, or for controlling rice diseases, such as against the causative organisms of rice blast disease (*Pyricularia oryzae*).

In protection of materials, the substances of the invention may be used to protect engineering materials against attack and destruction by undesirable microorganisms.

Engineering materials are taken to mean, in the present context, non-living materials which have been prepared for use in engineering. For example, engineering materials which are to be protected from microbial change or destruction by active compounds of the invention can be adhesives, sizes, paper and card, textiles, leather, wood, coatings and plastic articles, lubricant coolants and other materials which can be attacked or decomposed by microorganisms. In the context of materials to be protected, parts of production plants, for example cooling water circuits, may also be mentioned, which can be adversely affected by multiplication of microorganisms. In the context of the present invention, engineering materials which may be mentioned are preferably adhesives, sizes, papers and cards, leather, wood, coatings, lubricant coolants and heat transfer fluids, particularly preferably wood.

Microorganisms which can effect a degradation or change of the industrial materials which may be mentioned by way of example are bacteria, fungi, yeasts, algae and slime-forming organisms. Preferably, the active compounds of the invention are active against fungi, in particular moulds, wood-staining and wood-destroying fungi (Basidiomycetes) and against slime-forming organisms and algae.

Microorganisms of the following genera may be mentioned by way of example:

Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Scierophoma, such as *Scierophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

The active compounds, depending on their individual physical and/or chemical properties, can be converted into conventional formulations, such as solutions, emulsions, suspensions, powders, foams, pastes, granules, aerosols, very fine materials encapsulated in polymers and in coatings for seeds, and ultra low volume cold and hot mist spray formulations.

These formulations may be prepared in a known manner, e.g. by mixing the active compounds with extenders, that is liquid solvents, pressurized liquid gases and/or solid carriers, with or without the use of surface-active agents, that is emulsifiers and/or dispersants and/or foaming agents. If water is used as an extender, for example, organic solvents such as alcohols can also be used as solubilizer. Liquid solvents which are primarily useful are: aromatics, such as xylene, toluene or alkylnaphthalene, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol, and their ethers and esters, ketones, such as acetone, methyl ethyl ketone, methyl isobutyl ketone or cyclohexanone, highly polar solvents, such as dimethylformamide and dimethyl sulphoxide, and water; liquified gaseous extenders or carriers are taken to mean those liquids which are gaseous at room temperature and at atmospheric pressure, e.g. aerosol propellant gases, such as halogenated hydrocarbons and butane, propane, nitrogen and carbon dioxide; solid carriers which are suitable are: e.g., natural rock flours, such as kaolins, aluminas, talcum, chalk, quartz, attapulgite, montmorillonite or diatomaceous earths and synthetic rock flours, such as highly disperse silica, aluminium oxide and silicates; solid carriers for granules which are suitable are: e.g., crushed and fractionated natural rocks such as calcite, marble, pumice, sepiolite, dolomite and synthetic granules of inorganic and organic flours and granules of organic material such as sawdust, coconut shells, corn cobs and tobacco stalks; emulsifiers and/or foaming agents which are useful are: e.g., nonionic and anionic emulsifiers, such as polyoxyethylene fatty acid esters, polyoxyethylene fatty alcohol ethers, e.g. alkylaryl polyglycol ethers, alkylsulphonates, alkyl sulphates, arylsulphonates and protein hydrolysates; dispersants which are useful are: e.g., waste lignin-sulphite liquors and methylcellulose.

In the formulations, deposit builders can be used, such as carboxymethylcellulose, natural and synthetic pulverulent, granular or latex-form polymers, such as gum arabic, poly(vinyl alcohol), poly(vinyl acetate), and natural phospholipids, such as cephalins and lecithins, and synthetic phospholipids. Other additives can be mineral and vegetable oils.

In the formulations, colorants can be used, such as inorganic pigments, e.g. iron oxide, titanium oxide, Prussian blue, and organic colorants, such as alizarin, azo- and metallophthalocyanin colorants and trace nutrients such as salts of iron, manganese, boron, copper, cobalt, molybdenum and zinc.

In crop protection, the formulations generally contain between 0.1 and 95 per cent by weight of active compound, preferably between 0.5 and 90%.

The active compounds of the invention, when employed in crop protection, can be used in the formulations in a mixture with known fungicides, bactericides, acaricides, nematicides or insecticides, in order to increase in this manner, e.g., the activity spectrum or to prevent development of resistance.

The following substances, for example, are suitable for the mixtures.

Fungicides:
- 2-Aminobutane; 2-anilino-4-methyl-6-cyclopropyl-pyrimidine; 2',6'-dibromo-2-methyl-4'-trifluoromethoxy-4'-trifluoro-methyl-1,3-thiazolo-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoxyimino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate,
- calcium polysulphide, captafol, captan, carbendazim, carboxin, quinomethionate, chloroneb, chloropicrin, chlorothalonil, chlozolinate, cufraneb, cymoxanil, cyproconazole, cyprofurarn,
- dichlorophen, diclobutrazol, dichlofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridazole,
- fenarimol, fenbuconazole, fenfuram, fenitropan, fenpiclonil, fenpropidin, fenpropimorph, fentin acetate, fentin hydroxyd, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol,
- imazalil, imibenconazole, iminoctadine, iprobenfos (IBP), iprodione, isoprothiolane,
- kasugamycin, copper preparations, such as: copper hydroxide, copper naphthenate, copper oxychloride, copper sulphate, copper oxide, oxine-copper and Bordeaux mixture,
- mancopper, mancozeb, maneb, mepanipyrim, mepronil, metalaxyl, metconazole, methasulfocarb, methfuroxam, metiram, metsulfovax, myclobutanil, nickel-dimethyldithiocarbamate, nitrothal-isopropyl, nuarimol, ofurace, oxadixyl, oxamocarb, oxycarboxin,
- pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon,
- quintozene (PCNB),
- sulphur and sulphur preparations,
- tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole,
- validamycin A, vinclozolin,
- zineb, ziram.

Bactericides:
Bronopol, dichlorophen, nitrapyrin, nickel-dimethyldithiocarbamate, kasugamycin, octhilinone, furancarboxylic acid, oxytetracycline, probenazole, streptomycin, tecloftalam, copper sulphate and other copper preparations.

Insecticides/acaricides/nematicides:
- Abamectin, AC 303 630, acephate, acrinathrin, alanycarb, aldicarb, alphamethrin, amitraz, avermectin, AZ 60541, azadirachtin, azinphos A, azinphos M, azocyclotin, *Bacillus thuringiensis*, bendiocarb, benfuracarb, bensultap, beta-cyfluthrin, bifenthrin, BPMC, brofenprox, bromophos A, bufencarb, buprofezin, butocarboxim, butylpyridaben,
- cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate,
- dimethylvinphos, dioxathion, disulfoton,
- edifenphos, emamectin, esfenvalerate, ethiofencarb, ethion, ethofenprox, ethoprophos, etrimfos,
- fenamiphos, fenazaquin, fenbutatin oxide, fenitrothion, fenobucarb, fenothiocarb, fenoxycarb, fenpropathrin, fenpyrad, fenpyroximat, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox,
- imidacloprid, iprobenfos, isazofos, isofenphos, isoprocarb, isoxathion, ivermectin, lambda-cyhalothrin, lufenuron,
- malathion, mecarbam, mevinphos, mesulfenfos, metaldehyde, methacrifos, methamidophos, methidathion, methiocarb, methomyl, metolcarb, milbemectin, monocrotophos, moxidectin,
- naled, NC 184, NI 25, nitenpyram,
- omethoate, oxamyl, oxydemeton M, oxydeprofos,
- parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyraclofos, pyridaphenthion, pyresmethrin, pyrethrum, pyridaben, pyrimidifen, pyriproxyfen, quinalphos,

RH 5992,

Salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiometon, thionazin, thuringiensin, tralomethrin, triarathene, triazophos, triazuron, trichlorfon, triflumuron, trimethacarb, vamidothion, XMC, xylylcarb, zetamethrin.

A mixture with other known active compounds, such as herbicides, or with fertilizers and growth regulators is also possible.

The active compounds can be used as such, in the form of their formulations or the application forms prepared therefrom, such as ready to use solutions, suspensions, spray powders, pastes, soluble powders, dusting powders and granules. They are applied in a conventional manner, e.g. by pouring, spraying, atomizing, scattering, dusting, foaming, coating etc. It is also possible to discharge the active compounds by the ultra low volume method or to inject the active compound preparation or the active compound itself into the soil. Seeds of plants can also be treated.

When plant parts are treated, the active compound concentrations in the application forms can be varied in a relatively wide range: they are generally between 1 and 0.0001% by weight, preferably between 0.5 and 0.001% by weight.

When seeds are treated, active compound rates generally of 0.001 to 50 g per kilogram of seeds are needed, preferably 0.01 to 10 g.

When soil is treated, active compound concentrations of 0.00001 to 0.1% by weight, preferably 0.0001 to 0.02% by weight, at the site of action are necessary.

The compositions used for the protection of engineering materials generally contain the active compound in an amount of 1 to 95%, preferably 10 to 75%.

The application concentrations of the active compounds of the invention depend on the type and occurrence of the microorganisms to be controlled and on the composition of the material to be protected. The optimal application rate can be determined by series of tests. Generally, the application concentrations are in the range from 0.001 to 5% by weight, preferably 0.05 to 1.0% by weight, based on the material to be protected.

The efficiency and activity spectrum of the active compounds of the invention to be used in material protection, or of the compositions, concentrates or quite generally formulations which can be prepared therefrom can be increased if other antimicrobial active compounds, fungicides, bactericides, herbicides, insecticides or other active compounds to enhance the efficiency spectrum or achieve particular effects, such as additional protection from insects, are added, if appropriate. These mixtures can have a broader efficiency spectrum than the compounds of the invention.

In many cases, synergistic effects are achieved by this, i.e. the efficiency of the mixture is greater than the efficiency of the individual components. The following compounds, for example, are particularly expedient mixing partners:

sulfenamides, such as dichlofluanid, tolylfluanid, folpet, fluorfolpet;

benzimidazoles such as carbendazim (MBC), benomyl, fuberidazole, thiabendazole or their salts;

thiocyanates such as thiocyanatomethylthiobenzothiazole (TCMTB), methylenebisthiocyanate (MBT);

quaternary ammonium compounds such as benzyldimethyltetradecylammonium chloride, benzyl-dimethyl-dodecyl-ammonium chloride, dodecyl-dimethyl-ammonium chloride;

morpholine derivatives such as $C_{11}$–$C_{14}$-4-alkyl-2,6-dimethyl-morpholine homologs (tridemorph), (±)-cis-4-[3-(4-tert-butylphenyl)-2-methylpropyl]-2,6-dimethyl-morpholine (fenpropimorph), falimorph;

phenols, such as o-phenylphenol, tribromophenol, tetrachlorophenol, pentachlorophenol, 3-methyl-4-chlorophenol, dichlorophen, chlorphen or their salts;

azoles, such as triadimefon, triadimenol, bitertanol, tebuconazole, propiconazole, azaconazole, hexaconazole, prochloraz, cyproconazole, 1-(2-chlorophenyl)-2-(1-chlorocyclopropyl)-3-(1,2,4-triazol-1-yl)-propan-2-ol or 1-(2-chlorophenyl)-2-(1,2,4-triazol-1-yl-methyl)-3,3-dimethyl-butan-2-ol.

Iodopropargyl derivatives such as iodopropargyl butylcarbamate (IPBC), iodopropargyl chlorophenylfornal, iodopropargyl phenylcarbamate, iodopropargyl hexylcarbamate, iodopropargyl cyclohexylcarbamate, iodopropargyl oxyethylphenylcarbamate;

iodine derivatives such as diiodomethyl p-arylsulphones, e.g. diiodomethyl p-tolylsulphone; bromine derivatives such as bromopol;

isothiazolines, such as N-methylisothiazolin-3-one, 5-chloro-N-methylisothiazolin-3-one, 4,5-dichloro-N-octylisothiazolin-3-one, N-octylisothiazolin-3-one (octilinone);

benzisothiazolinones, cyclopentenisothiazolines; pyridines, such as 1-hydroxy-2-pyridinethione (and their Na, Fe, Mn, and Zn salts), tetrachloro 4-methylsulphonylpyridine;

metal soaps, such as the naphthenates, octoates, 2-ethylhexanoates, oleates, phosphates and benzoates of tin, copper and zinc, oxides, such as TBTO, $Cu_2O$, CuO, ZnO;

organotin compounds such as tributyltin naphthenate and tributyltin oxide;

dialkyldithiocarbamates such as Na salts and Zn salts of dialkyldithiocarbamates, tetramethylthiuram disulphide (TMTD);

nitriles, such as 2,4,5,6-tetrachloroisophthalonitrile (chlorothalonil) and other microbicides having an activated halogen group such as Cl—Ac, MCA, tectamer, bromopol, bromidox;

benzothiazoles, such as 2-mercaptobenzothiazoles; see above dazomet;

quinolines, such as 8-hydroxyquinoline;

formaldehyde-releasing compounds, such as benzyl alcohol mono(poly)hemiformal, oxazolidines, hexahydro-s-triazines, N-methylolchloroacetamide;

tris-N-(cyclohexyldiazeniumdioxy)-aluminium, N-(cyclohexyldiazeniumdioxy)-tri-butyltin or K salts, bis-(N-cyclohexyl)diazinium-(dioxy-copper or aluminium).

Insecticides which are preferably added are:

phosphoric esters such as azinphos-ethyl, azinphos-methyl, 1-(4-chlorophenyl)-4-(O-ethyl, S-propyl) phosphoryloxypyrazole (TIA-230), chlorpyrifos, coumaphos, demeton, demeton-S-methyl, diazinon, dichlorvos, dimethoate, ethoprophos, etrimfos, fenitrothion, fenthion, heptenophos, parathion, parathion-methyl, phosalone, phoxim, pirimiphos-ethyl, pirimiphos-methyl, profenofos, prothiofos, sulprofos, triazophos and trichlorfon.

Carbamates, such as aldicarb, bendiocarb, BPMC (2-(1-methylpropyl)phenyl methylcarbamate), butocarboxim, butoxycarboxim, carbaryl, carbofuran, carbosulfan, cloethocarb, isoprocarb, methomyl, oxamyl, pirimicarb, promecarb, propoxur and thiodicarb.

Pyrethroids, such as allethrin, alphamethrin, bioresmethrin, bifenthrin (FMC 54800), cycloprothrin, cyfluthrin, decamethrin, cyhalothrin, cypermethrin, deltamethrin, alpha-cyano-3-phenyl-2-methylbenzyl-2,2-dimethyl-3-(2-chloro-2-trifluoro-methylvinyl) cyclopropanecarboxylate, fenpropathrin, fenfluthrin, fenvalerate, flucythrinate, flumethrin, fluvalinate, permethrin and resmethrin; nitroimino and nitromethylene compounds, such as 1-[(6-chloro-3-pyridinyl)-methyl]-4,5-dihydro-N-nitro-1H-imidazole-2-amine (imidacloprid).

Organosilicon compounds, preferably dimethyl(phenyl) silylmethyl 3-phenoxybenzyl ethers, such as dimethyl-(4-ethoxyphenyl)-silylmethyl 3-phenoxybenzyl ether, or dimethyl(phenyl)-silylmethyl 2-phenoxy-6-pyridylmethyl ethers, such as dimethyl(9-ethoxyphenyl)-silylmethyl 2-phenoxy-6-pyridylmethyl ether or (phenyl)[3-(3-phenoxyphenyl)propyl](dimethyl)-silanes, such as (4-ethoxyphenyl)-[3(4-fluoro-3-phenoxyphenyl)-propyl] dimethylsilane.

Other active compounds which are suitable are algicides, moluscicides and compounds active against "sea animals", which colonize, for example, ship bottom coatings.

Preparation and use of active compounds of the invention are illustrated by the following examples.

PREPARATION EXAMPLES

Example 1

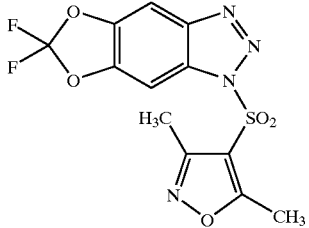

A mixture of 2.0 g (10 mmol) of 6,6-difluoro-[1,3]dioxolo [4,5-f]-1H-benzotriazole and 40 ml of absolute tetrahydrofuran is admixed at room temperature, with stirring, with 0.3 g (10 mmol) of sodium hydride (80% pure) and is then stirred for 10 minutes at room temperature. 1.9 g (10 mmol) of 3,5-dimethylisoxazole-4-sulphonyl chloride are then added and the mixture is stirred for 16 hours at 60° C. For work-up, the reaction mixture is poured into 20 ml of water. The resulting mixture is extracted twice, each time with 50 ml of ethyl acetate. The combined organic phases are dried over sodium sulphate and concentrated under reduced pressure. The remaining residue is chromatographed on silica gel with methylene chloride as mobile phase. 2.7 g (75% of theory) of 1-(3,5-dimethyl-isoxazole-4-sulphonyl)-6,6-difluoro-[1,3]dioxolo[4,5-f]-benzotriazole are obtained in this manner in the form of a colourless solid of melting point 120–123° C.

Example 2

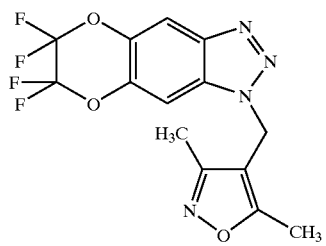

A mixture of 2.5 g (10 mmol) of 6,6,7,7-tetrafluoro-[1, 4]-dioxino[4,5-f]-1H-benzo-triazole and 40 ml of absolute tetrahydrofuran is admixed at room temperature, with stirring, with 0.3 g (10 mmol) of sodium hydride (80% pure) and is then stirred for 10 minutes at room temperature. 1.5 g (10 mmol) of 4-chloromethyl-3,5-dimethylisoazole are then added and the mixture is stirred for 18 hours at 60° C. For work-up, the reaction mixture is poured into 20 ml of water. The resulting mixture is extracted twice, each time with 50 ml of ethyl acetate. The combined organic phases are dried over sodium sulphate and concentrated under reduced pressure. The remaining residue is chromatographed on silica gel with diethyl ether as mobile phase. 1.4 g (40% of theory) of 1-(3,5-dimethylisoxazol-4-yl-methyl)-6,6,7,7-tetrafluoro-[1,4]dioxino[4,5-f]-1H-benzotriazole are obtained in this manner in the form of a red solid of melting point 144–148° C.

Example 3

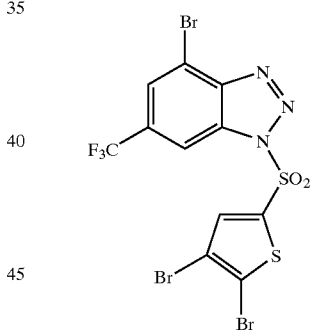

A mixture of 2.7 g (10 mmol) of 4-bromo-6-trifluromethyl-1H-benzotriazole and 40 ml of absolute tetrahydrofuran is admixed at room temperature, with stirring, with 0.3 g (10 mmol) of sodium hydride (80% pure) and is then stirred for 10 minutes at room temperature. 3.4 g (10 mmol) of 4,5-dibromothiophene-2-sulphonyl chloride are then added and the mixture is stirred for 16 hours at 60° C. For work-up, the reaction mixture is added to 200 ml of water. The resulting mixture is extracted twice, each time with 50 ml of ethyl acetate. The combined organic phases are dried over sodium sulphate and concentrated under reduced pressure. The remaining residue is chromatographed on silica gel with methylene chloride as mobile phase. 2.8 g (52% of theory) of 1-(3,4-dibromothien-2-yl-sulphonyl)-4-bromo-6-trifluoromethyl-1H-benzotriazole are obtained in this manner in the form of a colourless solid of melting point 192–195° C.

The substances of the formula

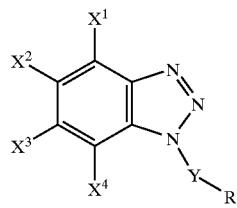

(I)

listed in Table 9 below are also prepared by the methods cited above.

TABLE 9

| Ex.-No. | $X^1$ | $X^2$ | $X^3$ | $X^4$ | Y | R | Melting point (° C.) |
|---|---|---|---|---|---|---|---|
| 4 | —H | | —O—CF$_2$CF$_2$—O— | —H | —SO$_2$— | 3,4,5-trimethylisoxazol-4-yl (H$_3$C, CH$_3$, CH$_3$) | 85 |
| 5 | —Br | —H | —CF$_3$ | —H | —SO$_2$— | 3,4,5-trimethylisoxazol-4-yl (H$_3$C, CH$_3$, CH$_3$) | 180–185 |
| 6 | —H | | —O—CF$_2$—CF$_2$—O— | —H | —SO$_2$— | 4,5-dimethylisoxazol-3-yl (CH$_3$, CH$_3$) | 116–120 |
| 7 | —H | | —O—CF$_2$—CF$_2$—O— | —H | —CO— | 3,4,5-trimethylisoxazol-4-yl (H$_3$C, CH$_3$, CH$_3$) | 70–74 |
| 8 | —H | | —O—CF$_2$—CF$_2$—O— | —H | —SO$_2$— | 2,3-dibromo-5-methylthiophene (Br, Br) | 185–188 |
| 9 | —H | | —O—CF$_2$—O— | —H | —SO$_2$— | 2,3-dibromo-5-methylthiophene (Br, Br) | 196–200 |
| 10 | —H | | —O—CF$_2$—O— | —H | —SO$_2$— | 5-chloro-1,3,4-trimethylpyrazole (H$_3$C, Cl, H$_3$C) | 178–182 |
| 11 | —H | | —O—CF$_2$—O— | —H | —SO$_2$— | 2-methylthiophene | 104–109 |
| 12 | —H | | —O—CF$_2$—CF$_2$—O— | —H | —SO$_2$— | 2-methylthiophene | 70–73 |

TABLE 9-continued
| Ex.-No. | X¹ | X² | X³ | X⁴ | Y | R | Melting point (° C.) |
|---|---|---|---|---|---|---|---|
| 13 | —H | | —O—CF₂—CF₂—O— | —H | —SO₂— | 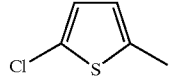 | 100–103 |
| 14 | —H | | —O—CF₂—O— | —H | —SO₂— | 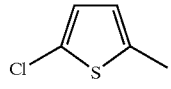 | 171–173 |
| 15 | —Br | —CF₃ | —H | —H | —SO₂— | 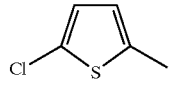 | 178–184 |
| 16 | —H | | —O—CF₂—O— | —H | —SO₂— | 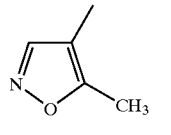 | 162–165 |
| 17 | —H | | —O—CF₂—O— | —H | —CO— | 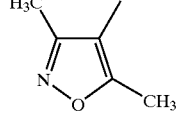 | 176–180 |
| 18 | —H | | —O—CF₂—CF₂—O— | —H | —CO— | 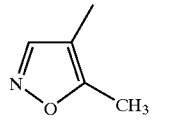 | 140–144 |
| 19 | —H | | —O—CF₂—O— | —H | —SO₂— | 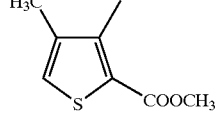 | 155–160 |
| 20 | —H | NO₂ | —H | —H | —SO₂— | 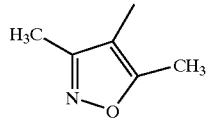 | 182–183 |
| 21 | —H | CH₃ | —H | —H | —SO₂— | 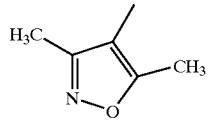 | 108–115 |
| 22 | —H | —H | —H | —H | —SO₂— | 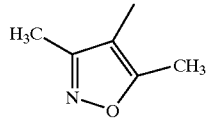 | 130–133 |
| 23 | —H | | —O—CF₂—O— | —H | —SO₂— | 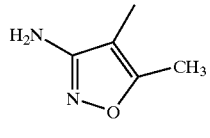 | 180–183 |
| 24 | —H | —H | —H | —H | —SO₂— | 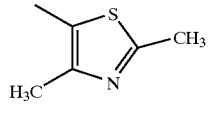 | *) |

TABLE 9-continued
| Ex.-No. | X¹ | X² | X³ | X⁴ | Y | R | Melting point (° C.) |
|---|---|---|---|---|---|---|---|
| 25 | —H | H₃C, H₃C, CH₃, CH₃ (2,4,4-trimethylpentyl) | | —H | —SO₂— | 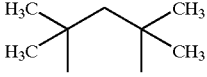 | 82–84 |
| 26 | —H | 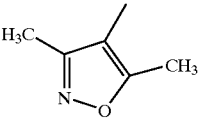 (fused benzo) | | —H | —SO₂— | 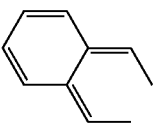 | 154–156 |
| 27 | —H | CH₃ | CH₃ | —H | —SO₂— | 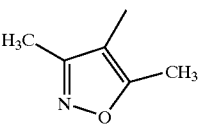 | 151–152 |
| 28 | —H | Cl | —H | —H | —SO₂— | 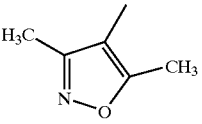 | 103–105 |
| 29 | —H | Cl | Cl | —H | —SO₂— | 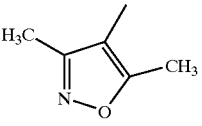 | 183–186 |
| 30 | —H | OCF₃ | Br | —H | —SO₂— | 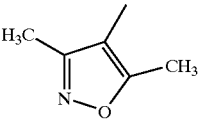 | 164–167 |
| 31 | —H | OCF₃ | Cl | —H | —SO₂— | 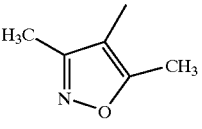 | 220 |
| 32 | —H | —OCF₂CFHO— | | —H | —SO₂— | 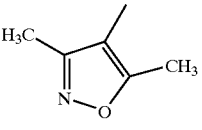 | 131–135 |
| 33 | —H | CF₃ | Cl | —H | —SO₂— | 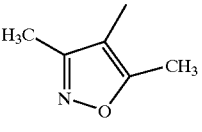 | 146–149 |

TABLE 9-continued

| Ex.-No. | X¹ | X² | X³ | X⁴ | Y | R | Melting point (° C.) |
|---|---|---|---|---|---|---|---|
| 34 | —H | | —OCF$_2$CF$_2$O— | —H | —SO$_2$— | 3-amino-4-methyl-5-methyl-isoxazole | 150–153 |
| 35 | —H | | (H$_3$C)$_3$C-CH$_2$-C(CH$_3$)$_2$ | —H | —SO$_2$— | 3-amino-4-methyl-5-methyl-isoxazole | 190 |
| 36 | —H | CH$_3$ | —H | —H | —SO$_2$— | 3-amino-4-methyl-5-methyl-isoxazole | 170–173 |
| 37 | —H | —H | —H | —H | —SO$_2$— | 3-amino-4-methyl-5-methyl-isoxazole | 157–158 |
| 38 | —H | CH$_3$ | CH$_3$ | —H | —SO$_2$— | 3-amino-4-methyl-5-methyl-isoxazole | 200–204 |
| 39 | —H | Cl | —H | —H | —SO$_2$— | 3-amino-4-methyl-5-methyl-isoxazole | 150–155 |
| 40 | —H | | fused benzo | —H | —SO$_2$— | 3-amino-4-methyl-5-methyl-isoxazole | 205–208 |
| 41 | —H | NO$_2$ | —H | —H | —SO$_2$— | 3-amino-4-methyl-5-methyl-isoxazole | 185–190 |
| 42 | Br | —H | CF$_3$ | —H | —SO$_2$— | 4-methyl-5-methyl-isoxazole | 160 |

TABLE 9-continued

| Ex.-No. | $X^1$ | $X^2$ | $X^3$ | $X^4$ | Y | R | Melting point (° C.) |
|---|---|---|---|---|---|---|---|
| 43 | $NO_2$ | —H | —H | —H | —$SO_2$— | 3,4-dimethylisoxazol-5-yl (H₃C on 3-position, CH₃ on 5-position, 4-methyl) | 173–174 |
| 44 | $CF_3$ | —H | Br | —H | —$SO_2$— | 3,4-dimethylisoxazol-5-yl | 140–143 |
| 45 | $NO_2$ | —H | —H | —H | —$SO_2$— | 3-amino-4-methylisoxazol-5-yl ($H_2N$ on 3-position, CH₃ on 5-position) | 170–174 |
| 46 | Br | —H | $CF_3$ | —H | —$SO_2$— | 3-amino-4-methylisoxazol-5-yl | 220 |
| 47 | Cl | Cl | Cl | Cl | —$SO_2$— | 3,4-dimethylisoxazol-5-yl | 210–214 |
| 48 | H | Cl | Cl | H | —$SO_2$— | 3-amino-4-methylisoxazol-5-yl | 196–199 |
| 49 | H | H | 6-methoxy-5-(trifluoromethyl)pyridin-3-yl (linked via O) | H | —$SO_2$— | 3,4-dimethylisoxazol-5-yl | 148–151 |
| 50 | H | H | H | H | —$SO_2$— | 5-cyclopropyl-3-methyl-4-isoxazolyl (H₃C on 3-position, cyclopropyl on 5-position) | 105–109 |

*) The compound cited in Example 24 is an oil. The substance is characterized by the mass spectrum.

MS: m/Z 294, 225, 201, 176, 135, 112, 106, 71, 45.

USE EXAMPLES

Example A
Material Protection Test

To demonstrate the activity against fungi, the minimal inhibitory concentrations (MIC values) are determined of compounds of the invention:

active compounds of the invention are added at concentrations of 0.1 mg/l to 5000 mg/l to an agar prepared with malt extract. After the agar has solidified, it is infected with pure cultures of *Penicillium brevicaule*, *Chaetomium globosum* and *Aspergillus niger*. After storage for two weeks at 28° C. and 60 to 70% relative humidity, the minimal inhibitory concentration (MIC value) is determined. The MIC value characterizes the lowest concentration of active compound at which there is no growth of the microbial species used.

Active compounds and results of experiments can be taken from the Table below.

TABLE A

Material protection test

| Active compound | Minimal inhibitory concentration (MIC value) in mg/l | | |
|---|---|---|---|
| | Penicillium brevicaule | Chaetomium globosum | Aspergillus niger |
| According to the invention: | | | |
| 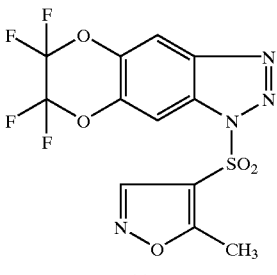 (6) | 200 | 100 | 200 |
| 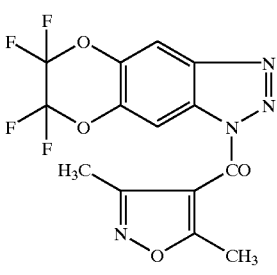 (7) | 200 | 100 | 400 |

Example B

Phytophthora Test (Tomato)/Protective

Solvent: 4.7 parts by weight of acetone
Emulsifier: 0.3 parts by weight of alkylaryl polyglycol ether To obtain an expedient preparation of active compound, 1 part by weight of active compound is mixed with the amounts of solvent and emulsifier cited and the concentrate is diluted with water to the desired concentration.

To test for protective activity, young plants are sprayed with the active compound preparation until moist. After the sprayed coating has dried on, the plants are inoculated with an aqueous spore suspension of *Phytophthora infestans*.

The plants are set up in an incubation cabinet at 100% relative humidity and approximately 20° C.

The evaluation is performed 3 days after the inoculation. In the evaluation, 0% denotes an efficiency corresponding to that of the control, while an efficiency of 100% denotes that no contamination is observed.

Active compounds, active compound concentrations and results of experiments can be taken from the Tables below.

TABLE B-1

Phytophthora test (tomato)/protective

| Active compound | Efficiency in %, based on the untreated control at an active compound concentration of 100 ppm |
|---|---|
| According to the invention: | |
| 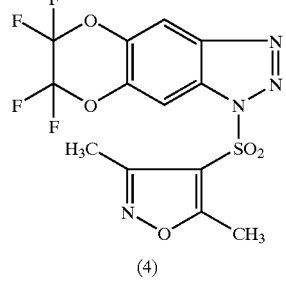 (4) | 94 |
| 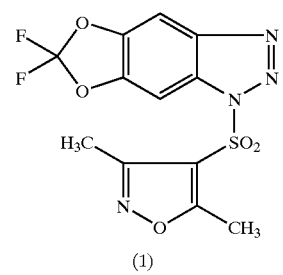 (1) | 94 |
| 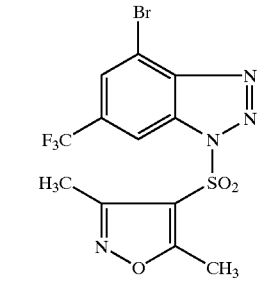 (5) | 95 |
| 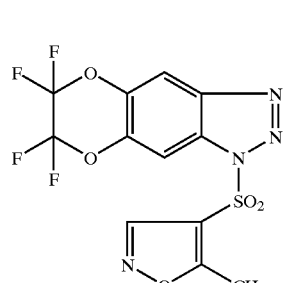 (6) | 94 |

TABLE B-1-continued

Phytophthora test (tomato)/protective

| Active compound | Efficiency in %, based on the untreated control at an active compound concentration of 100 ppm |
|---|---|
| (16) | 99 |

TABLE B-2

Phytophthora test (tomato)/protective

| Active compound | Efficiency in %, based on the untreated control at an active compound concentration of 50 ppm |
|---|---|
| According to the invention: | |
| (4) | 95 |
| (1) | 99 |
| (5) | 89 |

TABLE B-2-continued

Phytophthora test (tomato)/protective

| Active compound | Efficiency in %, based on the untreated control at an active compound concentration of 50 ppm |
|---|---|
| (16) | 100 |
| (22) | 97 |
| (42) | 98 |
| (23) | 97 |
| (21) | 97 |

TABLE B-2-continued

Phytophthora test (tomato)/protective

| Active compound | Efficiency in %, based on the untreated control at an active compound concentration of 50 ppm |
|---|---|
| 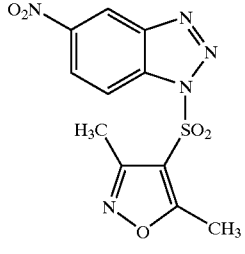 (20) | 100 |
| 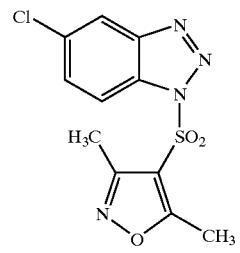 (28) | 100 |
| 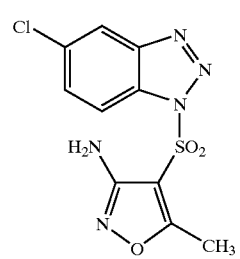 (39) | 97 |

Example C
Plasmopara Test (Grapevines)/Protective

Solvent: 4.7 parts by weight of acetone

Emulsifier: 0.3 parts by weight of alkylaryl polyglycol ether

To obtain an expedient preparation of active compound, 1 part by weight of active compound is mixed with the amounts of solvent and emulsifier cited and the concentrate is diluted with water to the desired concentration.

To test for protective activity, young plants are sprayed with the active compound preparation until dew moist. After the sprayed coating has dried on, the plants are inoculated with an aqueous spore suspension of *Plasmopara viticola* and then remain for 1 day in a moist chamber at 20 to 22° C. and 100% relative humidity. The plants are then set up for 5 days in a greenhouse at 21° C. and approximately 90% relative humidity. The plants are then moistened and placed in a moist chamber for 1 day.

The evaluation is performed 6 days after the inoculation. In the evaluation, 0% denotes an efficiency corresponding to that of the untreated control, while an efficiency of 100% denotes that no contamination is observed.

Active compounds, active compound concentrations and results of experiments can be taken from the Table below.

TABLE C

Plasmopara test (grapevines)/protective

| Active compound | Efficiency in %, based on the untreated control at an active compound concentration of 100 ppm |
|---|---|
| According to the invention: | |
| 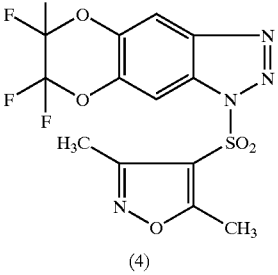 (4) | 100 |
| 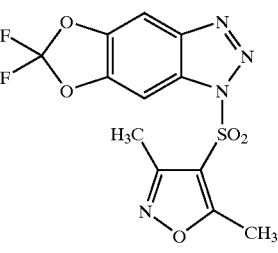 (1) | 100 |
| 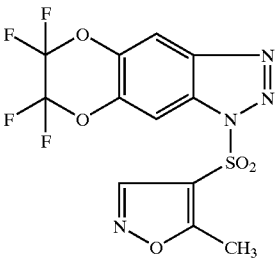 (6) | 100 |
| 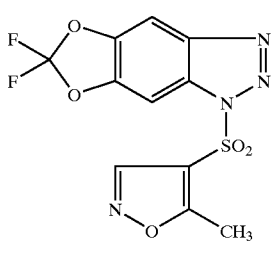 (16) | 100 |

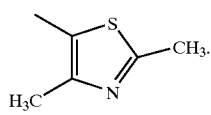

What is claimed is:
1. A benzotriazole of the formula

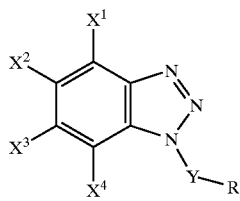

(I)

in which

X$^1$, X$^2$, X$^3$ and X$^4$, independently of each other, represent hydrogen, fluorine, chlorine, bromine, iodine, cyano, nitro, straight-chain or branched alkyl having 1 to 8 carbon atoms, straight-chain or branched halogenoalkyl having 1 to 6 carbon atoms and 1 to 13 identical or different halogen atoms, straight-chain or branched alkoxy having 1 to 8 carbon atoms, straight-chain or branched halogenoalkoxy having 1 to 6 carbon atoms and 1 to 13 identical or different halogen atoms, straight-chain or branched alkylthio having 1 to 8 carbon atoms, straight-chain or branched halogenoakylthio having 1 to 6 carbon atoms and 1 to 13 identical or different halogen atoms, straight-chain or branched alkylsulphinyl having 1 to 8 carbon atoms, straight-chain or branched halogenoalkylsulphinyl having 1 to 6 carbon atoms and 1 to 13 identical or different halogen atoms, straight-chain or branched alkylsulphonyl having 1 to 8 carbon atoms, straight-chain or branched halogenoalkylsulphonyl having 1 to 6 carbon atoms and 1 to 13 identical or different halogen atoms, cycloalkyl having 3 to 6 carbon atoms which may optionally be monosubstituted to pentasubstituted, identically or differently, by halogen and/or alkyl having 1 to 4 carbon atoms, hydroxycarbonyl, alkylcarbonyl having 1 to 6 carbon atoms in the straight-chain or branched alkyl moiety, alkoxycarbonyl having 1 to 6 carbon atoms in the straight-chain or branched alkoxy moiety, cycloalkylcarbonyl having 3 to 6 carbon atoms in the cycloalkyl moiety, cycloalkoxycarbonyl having 3 to 6 carbon atoms in the cycloalkyl moiety, —Z—R$^3$, wherein R$^3$ represents aryl having 6 to 10 carbon atoms, where each of these radicals can be monosubstituted to trisubstituted, identically or differently, by halogen, cyano, nitro, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, halogenoalkylthio having 1 to 4 carbon atoms and 1 to 5 identical or different halogen atoms, alkylsulphinyl having 1 to 4 carbon atoms, alkylsulphonyl having 1 to 4 carbon atoms, halogenoalkylsulphinyl having 1 to 4 carbon atoms and 1 to 5 identical or different halogen atoms and/or halogenoalkylsulphonyl having 1 to 4 carbon atoms and 1 to 5 identical or different halogen atoms, and Z represents a direct bond or CH$_2$, O, S, SO$_2$, CO, and
—CO—O—, where the oxygen atom is connected to the aryl radical, or
—SO$_2$—O—, where the sulphur atom is connected to the aryl radical, or
—S—CH$_2$—SO$_2$—, where the sulphur atom of the thio group is connected to the aryl radical, or X$^2$ and X 3 together represent an alkylene chain having 3 or 4 members which is optionally
monosubstituted to hexasubstituted by halogen, alkyl having 1 to 4 carbon atoms and/or halogenoalkyl having 1 to 4 carbon atoms and 1 to 9 halogen atoms, and in which alkylene chain one or two (non-adjacent) carbon atoms can be replaced by oxygen atoms, or X$^2$ and X$^3$ together represent a radical of the formula

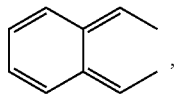

R represents thiazolyl where this radical can be monosubstituted or disubstituted, identically or differently, by fluorine, chlorine, bromine, cyano, nitro, amino, hydroxyl, formyl, carboxyl, carbamoyl, thiocarbamoyl, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, trifluoromethyl, difluoromethoxy, trifluoromethoxy, difluoromethylthio, trifluoromethylthio, trifluoromethylsulphinyl, trifluoromethylsulphonyl, cyclopropyl, methylamino, ethylamino, n- or i-propylamino, dimethylamino, diethylamino, acetyl, propionyl, methylcarbonylamino, acetyloxy, methoxycarbonyl, ethoxycarbonyl, methylsulphonyloxy, ethylsulphonyloxy, hydroxyiminomethyl, hydroxyiminoethyl, methoxyiminomethyl, ethoxyiminomethyl, methoxyiminoethyl and/or ethoxyiminoethyl and Y represents a —SO$_2$, —CO—O— or —SO—O, where in the case of the two last named groups, the carbon atom or the sulphur atom, respectively, is connected to the nitrogen atom of the triazole ring, or an addition product thereof with an acid or metal salt.

2. A microbiocidal composition comprising a microbiocidally effective amount of a benzotriazole of the formula (I) according to claim 1 or an acid addition salt or metal salt complex thereof in a mixture with an inert diluent.

3. A method for controlling undesirable microorganisms comprising applying to the microorganisms, to their habitat or to a place from which it is desired to exclude such microorganisms a microbiocidally effective amount of a benzotriazole of the formula (I) according to claim 1 or an acid addition salt or a metal salt complex thereof.

4. A benzotriazole of the formula (I) according to claim 1, wherein

X$^1$, X$^2$, X$^3$ and X$^4$ each represent hydrogen,

Y represents —SO$_2$—, and

R represents